(12) United States Patent
DuPuis et al.

(10) Patent No.: US 9,370,600 B1
(45) Date of Patent: Jun. 21, 2016

(54) ULTRAVIOLET LIGHT GERMICIDAL SANITIZING SYSTEM ULITILIZING VARIOUS ROOM SANITIZING MODES

(71) Applicant: Elevated Health System, LLC, Wichita, KS (US)

(72) Inventors: Ann Alexander DuPuis, Wichita, KS (US); John DuPuis, Wichita, KS (US)

(73) Assignee: Elevated Health System, LLC, Wichita, KS (US)

( * ) Notice: Subject to any disclaimer, the term of this patent is extended or adjusted under 35 U.S.C. 154(b) by 0 days.

(21) Appl. No.: 14/579,601

(22) Filed: Dec. 22, 2014

(51) Int. Cl.
*A61L 9/20* (2006.01)
*H05B 37/02* (2006.01)
*F21V 14/08* (2006.01)

(52) U.S. Cl.
CPC . *A61L 9/20* (2013.01); *F21V 14/08* (2013.01); *H05B 37/0227* (2013.01); *H05B 37/0281* (2013.01)

(58) Field of Classification Search
CPC ........... G05D 25/02; G05D 25/00; A61L 2/10
See application file for complete search history.

(56) References Cited

U.S. PATENT DOCUMENTS

| | | | | |
|---|---|---|---|---|
| 1,961,700 | A | | 6/1934 | Moehler |
| 4,748,545 | A | * | 5/1988 | Schmitt .......................... 362/219 |
| 5,330,722 | A | * | 7/1994 | Pick et al. .......................... 96/55 |
| 5,589,132 | A | * | 12/1996 | Zippel .............................. 422/24 |
| 5,788,940 | A | | 8/1998 | Cicha et al. |
| 5,861,633 | A | * | 1/1999 | Mandellos ................. 250/504 R |
| 6,283,612 | B1 | * | 9/2001 | Hunter .......................... 362/240 |
| 6,912,429 | B1 | * | 6/2005 | Bilger .............................. 700/19 |
| 7,791,044 | B1 | * | 9/2010 | Taylor et al. ............. 250/455.11 |
| 2005/0098553 | A1 | * | 5/2005 | Devine et al. ................. 219/411 |
| 2006/0120915 | A1 | * | 6/2006 | Lewandowski ................. 422/24 |
| 2007/0127244 | A1 | * | 6/2007 | Cunius .......................... 362/260 |
| 2008/0036580 | A1 | * | 2/2008 | Breed .......................... 340/438 |
| 2008/0079569 | A1 | * | 4/2008 | Axelsen ........................ 340/541 |
| 2008/0125940 | A1 | * | 5/2008 | Breed .............................. 701/45 |
| 2009/0004046 | A1 | * | 1/2009 | McEllen .......................... 422/2 |
| 2009/0117001 | A1 | * | 5/2009 | Hyde et al. ..................... 422/24 |
| 2009/0191100 | A1 | * | 7/2009 | Deal ............................ 422/105 |
| 2010/0032589 | A1 | | 2/2010 | Leben |
| 2010/0143205 | A1 | * | 6/2010 | Engelhard ..................... 422/121 |
| 2010/0187832 | A1 | * | 7/2010 | Holland et al. ............... 290/1 A |

(Continued)

OTHER PUBLICATIONS

International Search Report and Written Opinion for PCT Appln. No. PCT/US14/71972; Filed Dec. 22, 2014.

*Primary Examiner* — Robert Kim
*Assistant Examiner* — Sean Luck
(74) *Attorney, Agent, or Firm* — Hovey Williams LLP

(57) ABSTRACT

An ultraviolet (UV) light germicidal sanitizing system for use in an enclosed space comprises a room occupancy sensor, a door sensor, a UV light generating unit, and a control software application. The room occupancy sensor is positioned in the enclosed space and generates a first signal indicating that the enclosed space is either occupied or unoccupied. The room occupancy sensor is implemented with a door providing access to the enclosed space and generates a second signal indicating that the door is either open or closed. The UV light generating unit receives the first and second signals and generates UV light into the enclosed space if the first signal indicates that the enclosed space is unoccupied and the second signal indicates that the door is closed. The control software application generates commands for the UV light generating unit to start generating UV light and to stop generating UV light.

11 Claims, 13 Drawing Sheets

(56) References Cited

U.S. PATENT DOCUMENTS

| | | |
|---|---|---|
| 2010/0193510 A1* | 8/2010 | Danilychev .................. 219/756 |
| 2011/0066302 A1* | 3/2011 | McEwan ....................... 700/295 |
| 2011/0095895 A1* | 4/2011 | Chero et al. ................. 340/628 |
| 2011/0146705 A1* | 6/2011 | Hart et al. ......................... 134/2 |
| 2011/0168898 A1 | 7/2011 | Statham et al. |
| 2012/0078676 A1* | 3/2012 | Adams et al. ................ 705/7.22 |
| 2012/0086345 A1* | 4/2012 | Tran .............................. 315/158 |
| 2012/0126134 A1* | 5/2012 | Deal et al. ..................... 250/372 |
| 2012/0155073 A1* | 6/2012 | McCanless et al. .......... 362/218 |
| 2012/0310376 A1* | 12/2012 | Krumm et al. ................. 700/31 |
| 2013/0172963 A1* | 7/2013 | Moffat ............................. 607/94 |
| 2014/0044590 A1 | 2/2014 | Trapani |

\* cited by examiner

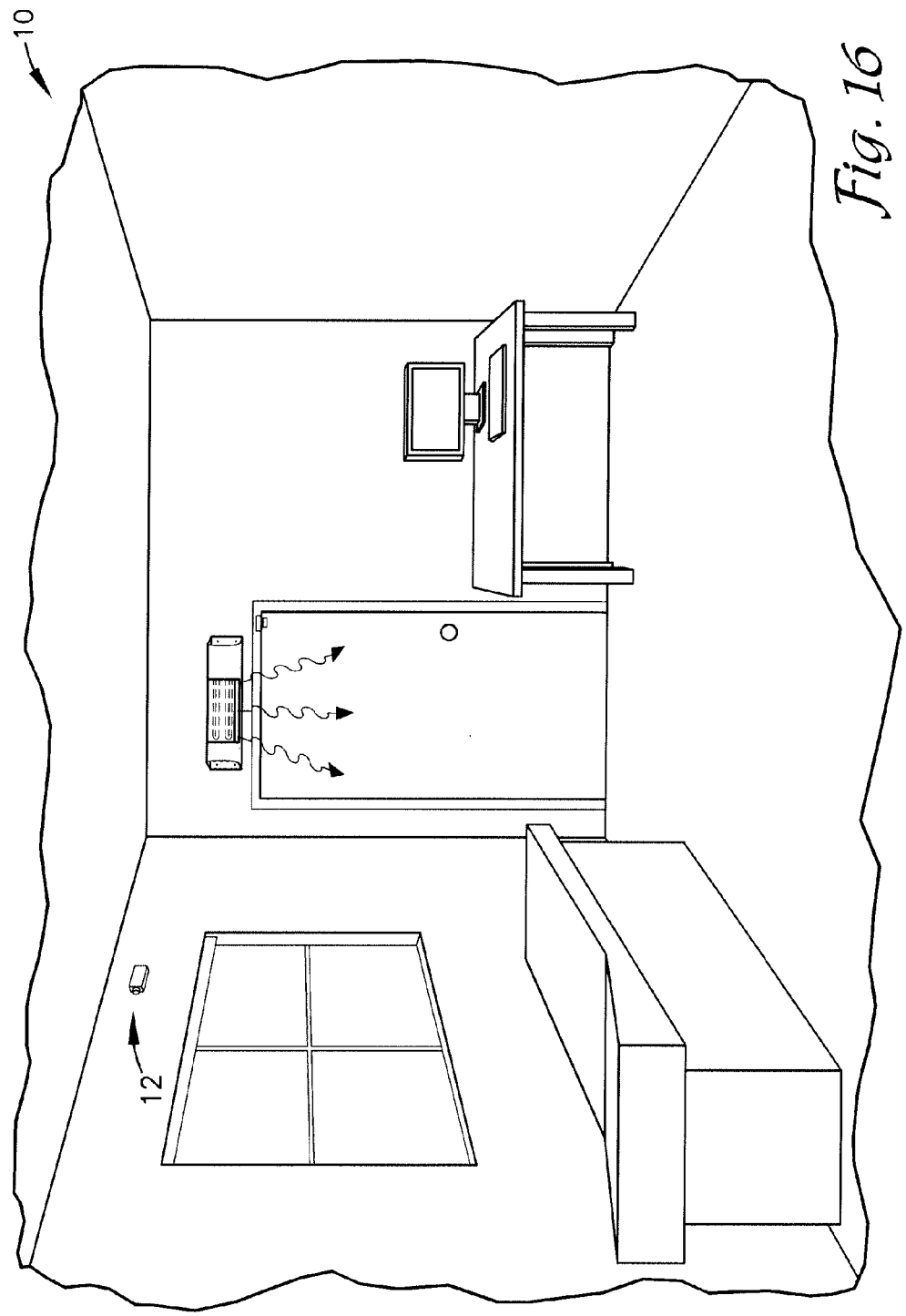

ULTRAVIOLET LIGHT GERMICIDAL SANITIZING SYSTEM ULITILIZING VARIOUS ROOM SANITIZING MODES

BACKGROUND OF THE INVENTION

1. Field of the Invention

Embodiments of the current invention relate to germicidal sanitizing systems that utilize ultraviolet light.

2. Description of the Related Art

Germicidal sanitizing with ultraviolet (UV) light generally involves exposing an area or an enclosed space to a UV light source. Due to the potentially harmful effects of UV light to humans, care must be taken when sanitizing a space to avoid human exposure.

SUMMARY OF THE INVENTION

Embodiments of the current invention solve the above-mentioned problems and provide a distinct advance in the art of germicidal sanitizing. More particularly, embodiments of the invention provide an ultraviolet (UV) light generating unit that includes a shutter to control the amount of UV light that is transmitted into an enclosed space. Embodiments of the invention may further provide a UV light germicidal sanitizing system that includes the UV light generating unit along with sensors to detect human presence and a control system responsive to the sensors to control the operation of the shutter.

Embodiments of the UV light generating unit comprise a housing, a shutter, a UV light source, a memory element, and a processing element. The housing includes a shell with an aperture. The shutter is movable between a first position in which the shutter covers the aperture and a second position in which the shutter exposes a majority of the aperture. The UV light source is positioned within the housing and generates radiation in the UVC band of the electromagnetic radiation spectrum through the aperture when the shutter is in the second position. The processing element is electronically coupled with the memory element. The processing element receives a first signal from a room occupancy sensor, wherein the first signal indicates that the enclosed space is either occupied or unoccupied. The processing element also generates a second signal to be used to move the shutter to the first position when the first signal indicates that the enclosed space is occupied and to the second position when the first signal indicates that the enclosed space is unoccupied.

A first embodiment of the UV light germicidal sanitizing system is intended for use in an enclosed space and comprises a room occupancy sensor, a door sensor, a UV light generating unit, a base station transceiver, and a control software application. The room occupancy sensor is positioned within the enclosed space and generates a first signal indicating that the enclosed space is either occupied or unoccupied. The door sensor monitors a door providing access to the enclosed space and generates a second signal indicating that the door is either open or closed. The UV light generating unit is positioned within the enclosed space. The UV light generating unit receives the first signal and the second signal and delivers UV light into the enclosed space if the first signal indicates that the enclosed space is unoccupied and the second signal indicates that the door is closed. The base station transceiver provides wireless communication with the UV light generating unit. The control software application executes on a computing device that is coupled with the base station transceiver and generates a first operating command for the UV light generating unit to start generating UV light and a second operating command for the UV light generating unit to stop generating UV light.

A second embodiment of the UV light germicidal sanitizing system is intended for use in a facility with a plurality of enclosed spaces and comprises a plurality of room occupancy sensors, a plurality of door sensors, and a plurality of UV light generating units. The room occupancy sensors are each positioned within one enclosed space and generate a first signal indicating that the enclosed space is either occupied or unoccupied. The door sensors each monitor a door providing access to one enclosed space and generate a second signal indicating that the door is either open or closed. The UV light generating units are each assigned a unique identifier and positioned within one enclosed space. The UV light generating units also each receive operating commands including identifiers from other UV light generating units and transmit the operating commands to other UV light generating units if the identifier does not match the unique identifier. In addition, the UV light generating units each receive the first signal and the second signal and generate UV light into the enclosed space if the first signal indicates that the enclosed space is unoccupied and the second signal indicates that the door is closed.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current invention will be apparent from the following detailed description of the embodiments and the accompanying drawing figures.

BRIEF DESCRIPTION OF THE DRAWING FIGURES

Embodiments of the current invention are described in detail below with reference to the attached drawing figures, wherein:

FIG. 16 is a perspective view of the UV light generating unit mounted above a doorway of the enclosed space shown in FIG. 1.

Figure 1:
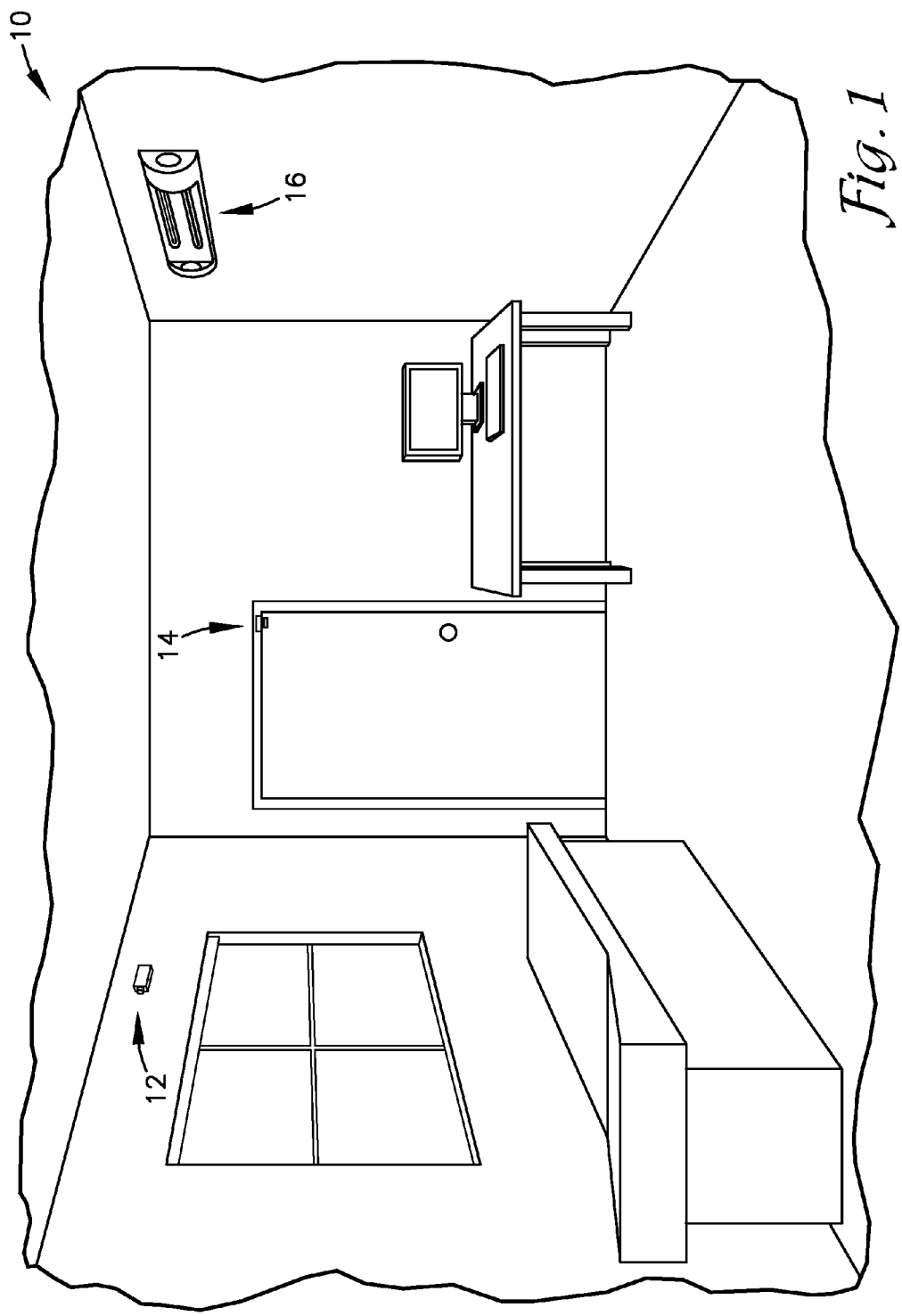
FIG. 1 is a perspective view of an ultraviolet (UV) light germicidal sanitizing system, constructed in accordance with a first embodiment of the current invention, utilized in an exemplary enclosed space of a medical exam room.

The drawing figures do not limit the current invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current technology can include a variety of combinations and/or integrations of the embodiments described herein.

An ultraviolet (UV) light germicidal sanitizing system 10, constructed in accordance with various embodiments of the current invention, is illustrated in FIG. 1. The system 10 may broadly comprise a room occupancy sensor 12, a door sensor 14, a UV light generating unit 16, a base station transceiver 18, and a control software application 20. The system 10 may interface with a computing device 22 that executes the control software application 20. The system 10 is typically utilized in a facility with a single enclosed space that needs germicidal sanitizing such as a single exam room in a doctor's office, a closet, a bathroom, an elevator, a laboratory, an operating room, and the like.

The room occupancy sensor 12, as seen in FIG. 1, generally detects the presence of people within the enclosed space in which the system 10 is utilized. In some embodiments, the room occupancy sensor 12 may include one or more motion detectors capable of detecting movement, particularly of humans. The motion detectors may include infrared, radio frequency (RF), ultrasonic, or similar technologies. In other embodiments, the room occupancy sensor 12 may include one or more thermal sensors capable of detecting infrared radiation, heat, or elevated temperatures. In yet other embodiments, the room occupancy sensor 12 may include one or more pressure sensors capable of detecting pressure or weight on an object or surface. The pressure sensors may include transducing elements that are implemented in pressure mats or scales which can be placed in objects such as a patient's bed or examining table, or on the floor under and around the objects. In various embodiments, the room occupancy sensor 12 may include combinations of two or more of the above-mentioned sensor types. Thus, the room occupancy sensor 12 may detect people in the enclosed space whether they are moving or still, hot or cold, on the examining table, in the patient's bed or on the floor. The room occupancy sensor 12 may generate a room occupancy signal indicating the presence or absence of at least one person in the enclosed space.

The door sensor 14, as seen in FIG. 1, generally determines whether a door that provides access to the enclosed space is closed or not closed. The door sensor 14 may include proximity switches, reed switch sensors, or the like. When a reed switch sensor is used, the sensor may include a reed switch positioned on the door frame and a magnet placed on the door. The reed switch is closed, or activated, only when the magnet is closely aligned therewith. Thus, the door sensor 14 can detect only whether the door is closed or not closed (at least partially open). Additional sensors or switches could be utilized to determine other positions of the door. In typical embodiments, a first door sensor 14 may be placed on the main entry door to the enclosed space. In other embodiments, a second door sensor 14 may be placed on another door, such as a bathroom or closet door, that access the enclosed space. Each door sensor 14 may generate a door closed signal indicating whether the door is closed or not closed.

The UV light generating unit 16, as seen in FIGS. 1-6, may include a housing 24, a shutter 26, a shutter motor 28, a shutter position sensor 30, an ultraviolet light source 32, an air circulation fan 34, a communication element 36, a memory element 38, and a processing element 40.

Figure 2:
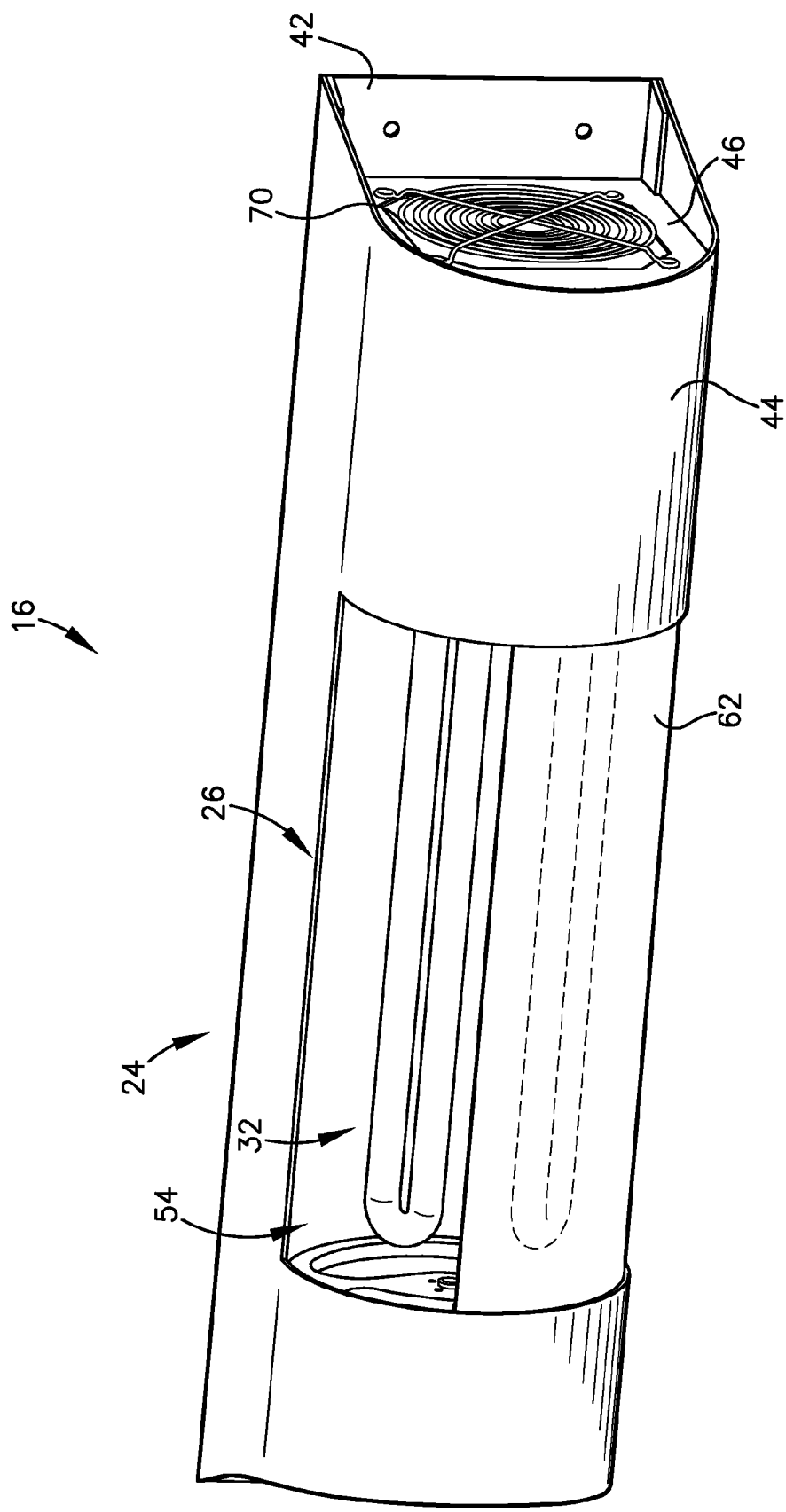
FIG. 2 is a top perspective view of a UV light generating unit including a shutter that is partially open to expose a UV light source.
Figure 3:
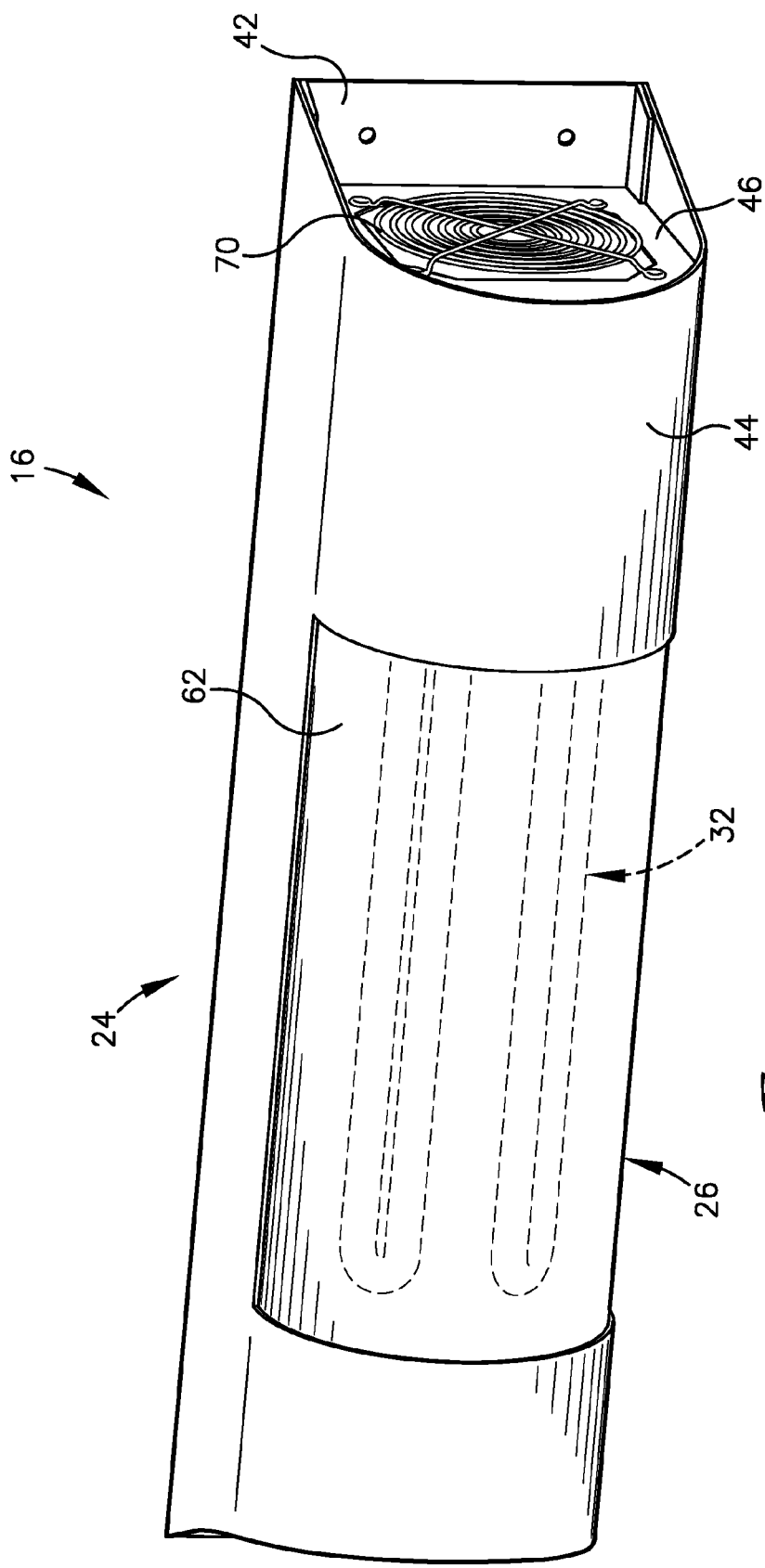
FIG. 3 is a top perspective view of the UV light generating source of FIG. 2 with the shutter fully closed.

The housing 24, best seen in FIGS. 2 and 3, generally houses the UV light source 32, the air circulation fan 34, and the shutter position sensor 30. An exemplary housing 24 may include a base plate 42, a shell 44, a first end wall 46, a second end wall 48, a first internal wall 50, and a second internal wall 52. The base plate 42 may be substantially planar. The shell 44 may have an elongated arch shape, or may form a portion of a cylinder or a semi-cylinder, with planar sidewalls that are attached to opposing edges of the base plate 42. The shell 44 may include an opening 54 or aperture along its curved, semi-cylindrical portion. The first and second end walls 46, 48 may be fastened to the base plate 42 proximal to opposing ends of the shell 44 such that the shell 44 covers the first and second end walls 46, 48. The first and second internal walls 50, 52 may be attached to the base plate 42 in the space between, and roughly parallel to, the first and second end walls 46, 48. In addition, the first internal wall 50 may include at least a first opening 56 and a second opening 58, while the second internal wall 52 may include at least a first opening 60.

The shutter 26, seen in FIGS. 2-5, generally serves as a UV light source 32 blocking component. The shutter 26 may be formed from material that is opaque or non-transmissive to electromagnetic radiation that has wavelengths in the UV range, i.e., wavelengths ranging from approximately 100 nanometers (nm) to approximately 400 nm. An exemplary material may include metals such as steel or aluminum. The shutter 26 may include a sidewall 62 with an arcuate or semi-cylindrical shape having a smaller radius of curvature than the curved portion of the shell 44. In various embodiments, an outer surface of the sidewall 62 may include a non-reflective coating, while an inner surface may remain uncoated. The sidewall 62 may have a length greater than the length of the opening 54 of the shell 44. The shutter 26 may also include a first arm 64 with a first end connected to one end of the sidewall 62 and a second arm 66 with a first end connected to an opposing end of the sidewall 62. The first and second arms 64, 66 may extend inward toward the center of curvature. A second end of the first arm 64 may be connected to the shutter motor 28, as described in more detail below. A second end of the second arm 66 may be rotatably connected to a roughly central point of the second internal wall 52.

In another embodiment, the shutter 26 may be integrated into the shell 44 of the housing 24 in place of the opening 54. The shutter 26 may be formed from opacity-adjustable materials such as smart glass, switchable glass, electric or electronic glass, liquid crystal glass, suspended particle devices, polymer dispersed liquid crystal devices, nanocrystals, micro blinds, and the like. In such embodiments, the shutter 26 may be transparent when provided with a first electrical characteristic, such as a first voltage. And, the shutter 26 may be opaque when provided with a second electrical characteristic, such as a second voltage. Furthermore, the shutter 26 may be configured such that a first portion of the shutter 26 may be adjusted to be opaque, while a second portion of the shutter 26 may be adjusted to be transparent.

Figure 4:
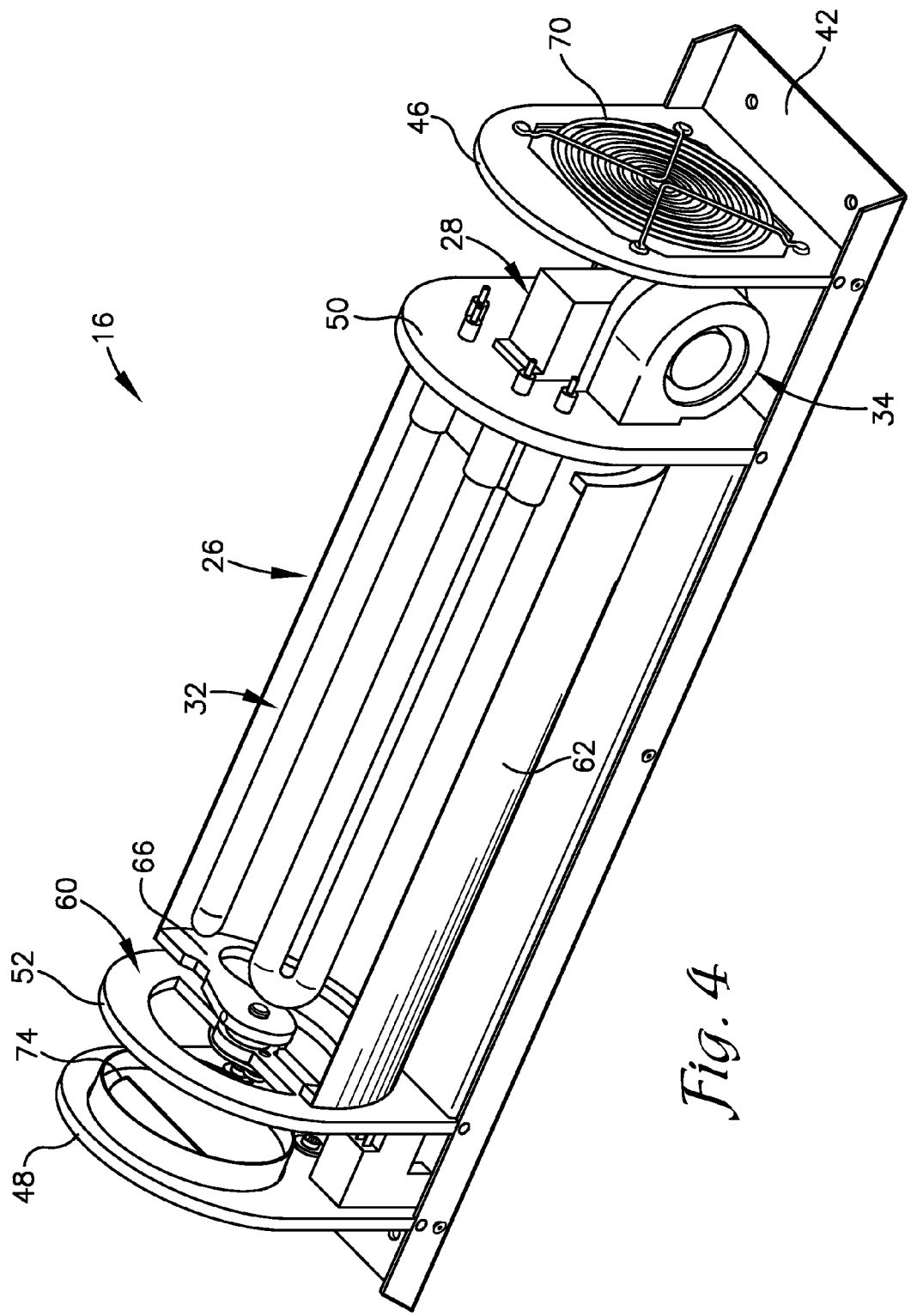
FIG. 4 is a perspective view of the UV light generating unit from a first end showing the unit with its shell removed to reveal its internal components.
Figure 5:
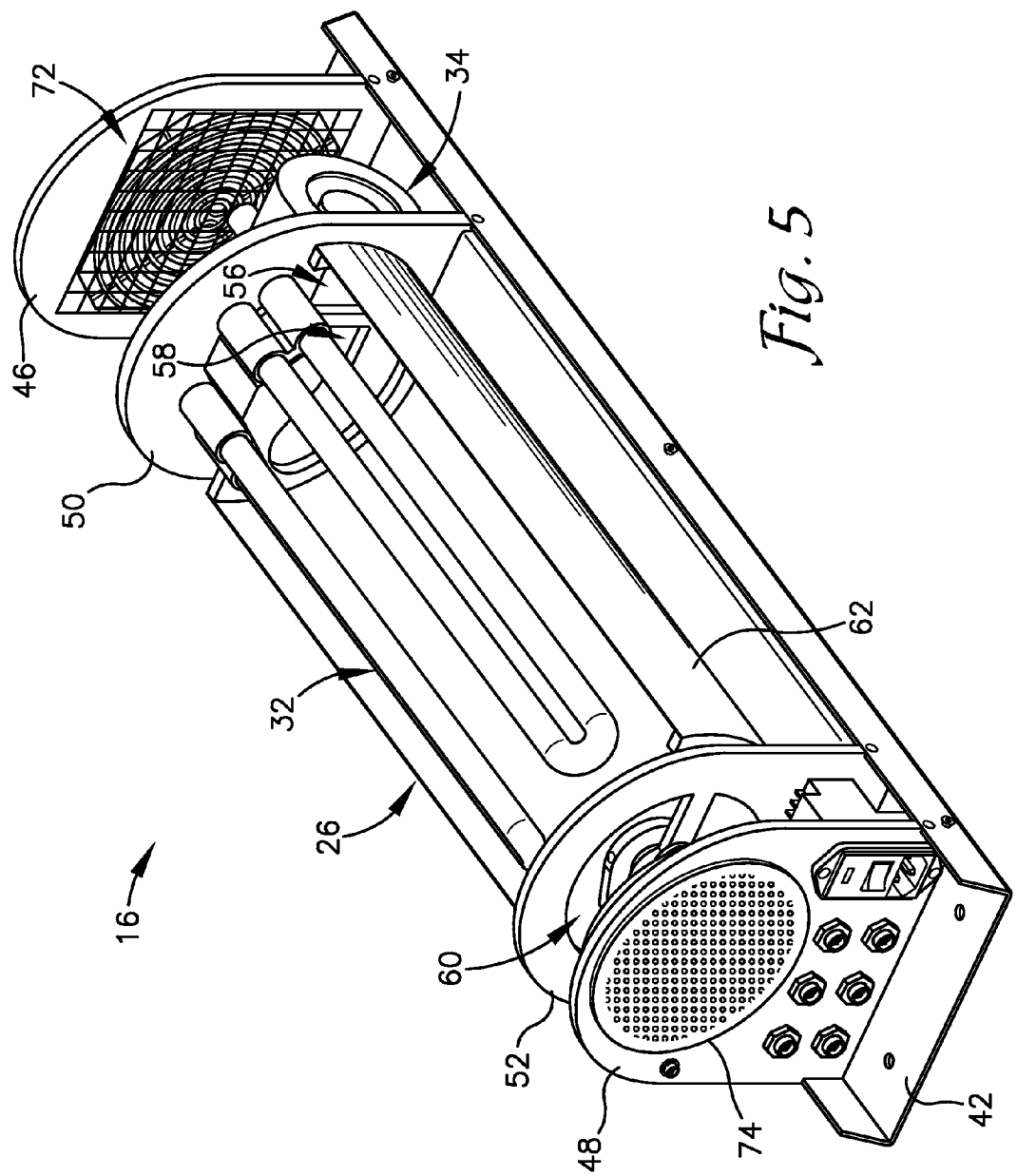
FIG. 5 is a perspective view of the UV light generating unit from a second end showing the unit with its shell removed.

The shutter motor 28, shown in FIGS. 4 and 5, generally adjusts the position of the shutter 26 and may include alternating current (AC) motors, direct current (DC) motors, stepper motors, brushless motors, and the like. An exemplary shutter motor 28 may include a servo motor. The shutter motor 28 may be mounted to an outer surface of the first internal wall 50. The shutter motor 28 may include a shaft that extends through the first opening 56 in the first internal wall 50 and connects to the first arm 64 of the shutter 26. The shutter motor 28 may be configured to generate rotation of the shutter 26 in a first direction to open the shutter 26 and in a second, opposing direction to close the shutter 26. In various embodiments, the shutter motor 28 may be able to open the shutter 26 in either direction, such as clockwise or counterclockwise. In addition, the shutter motor 28 may rotate the shutter 26 through an angular range of approximately 180 degrees.

Figure 6:
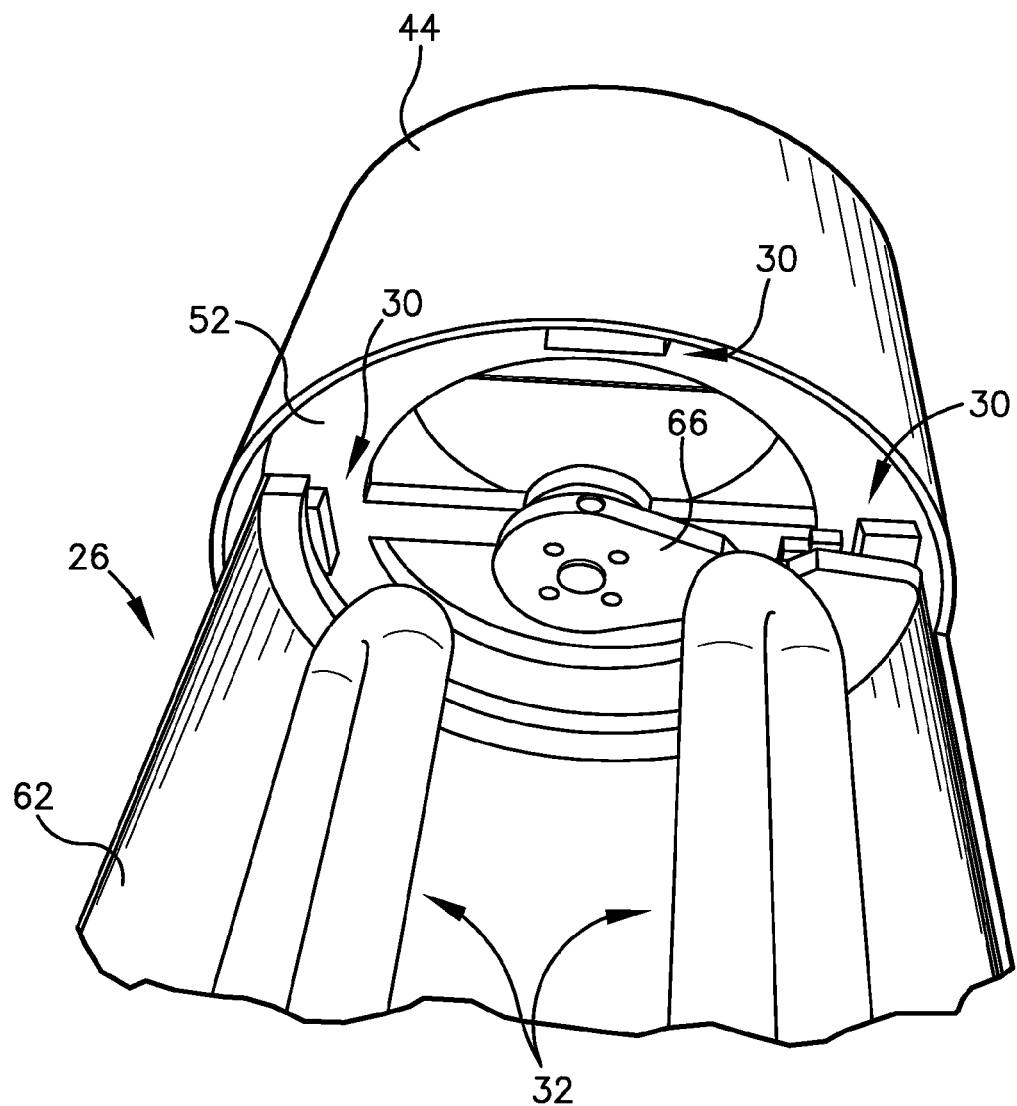
FIG. 6 is a perspective view of the interior of the UV light generating unit illustrating shutter position sensors that determine whether the shutter is open or closed.
Figure 7:
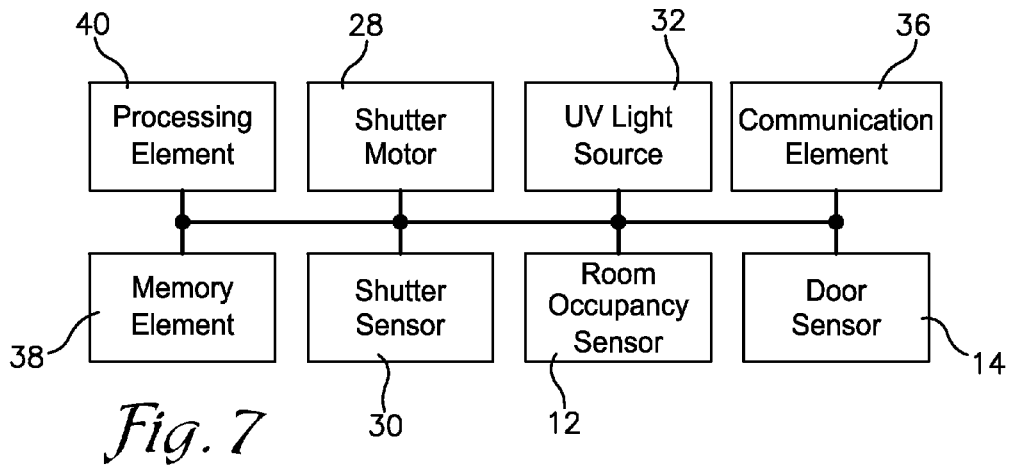
FIG. 7 is a schematic block diagram of components of the UV light germicidal sanitizing system.

The shutter position sensor 30, best seen in FIG. 6, generally determines whether the shutter 26 is open or closed. The shutter position sensor 30 may be any type of proximity switch that is activated when two objects are close to one another. An exemplary shutter position sensor 30 may include a reed switch sensor with one magnet and three reed switches. The magnet may be mounted on the sidewall 62 of the shutter 26 near the second internal wall 52. A first reed switch may be mounted on the second internal wall 52 in a location that aligns with the magnet when shutter 26 is fully closed. A second reed switch may be mounted on the second internal wall 52 in a location that aligns with the magnet when shutter 26 is approximately halfway open. A third reed switch may be mounted on the second internal wall 52 in a location that aligns with the magnet when shutter 26 is fully open. Thus, the shutter position sensor 30 may determine when shutter 26 is fully closed (corresponding to the first reed switch being activated), approximately halfway open (corresponding to the second reed switch being activated), or fully open (corresponding to the third reed switch being activated). The shutter position sensor 30 may generate a shutter position signal indicating whether the shutter 26 is closed, approximately halfway open, or fully open.

The UV light source 32, seen in FIGS. 1-5, generally provides a source of sanitizing, germicidal, and disinfecting radiation. The UV light source 32 may generate radiation with wavelengths in the UV range of the electromagnetic radiation spectrum—specifically, in the UVC range which includes wavelengths from approximately 100 nm to approximately 280 nm. An exemplary UV light source 32 may generate radiation with wavelengths that range from approximately 240 nm to approximately 280 nm—with a specific wavelength of approximately 254 nm. UV radiation with wavelengths in this range has been found to break down organic material found in the air in an indoor environment and alter or deconstruct DNA in living microorganisms, rendering them harmless or prohibiting growth and reproduction. The wavelength of the UV light source 32 is generally fixed when the source is manufactured, although in some embodiments, the wavelength of the UV light source 32 may be varied after installation, or during operation.

The UV light source 32 may include components configured to emit EM radiation in the UV range, such as light-emitting diodes, lasers, electric arc lamps, pressurized mercury bulbs, xenon lamps, or the like. An exemplary UV light source 14 includes two elongated U-shaped mercury bulbs. The bulbs may plug into sockets that are mounted on an inner surface of the first internal wall 50, such that the longitudinal axis of the UV light source 32 is aligned with the longitudinal axis of the housing 24. In addition, the UV light source 32 may include electrical or electronic components, such as a ballast, that adjust and maintain the voltage or other electrical properties for the UV light source 32.

The air circulation fan 34, best seen in FIG. 4, generally moves air through the UV light generating unit 16 to provide germicidal sanitation or disinfection of the air in a room, or the air in the vicinity of the UV light generating unit 16. The air circulation fan 34 may include rotary fans or blowers as are known in the art. An exemplary air circulation fan 34 may include a rotary impeller type of fan. The air circulation fan 34 may be mounted to the outer surface of the first internal wall 50 such that the air output of the air circulation fan 34 may flow through the second opening 58 in the first internal wall 50.

Accompanying the air circulation fan 34 may be a grill 70, an air filter 72, and a vent 74, seen in FIGS. 4 and 5. The grill 70 generally prevents large objects from entering the housing 24 and may include concentric-circle rods mounted on a pair of crossbars or similar grill structures. The grill 70 may be attached to an outer surface of the first end wall 46 and may cover an opening therein. The air filter 72 generally prevents smaller objects, such as dust, hair, etc., from entering the housing 24 and may include mesh material, foam material, screen material, combinations thereof, or the like. The air filter 72 may be attached to the grill 70 adjacent to the inner surface of the first end wall 46. The vent 74 generally provides an air exhaust port and may include a louvered structure that blocks or shields UV radiation generated by the UV light source 32. The vent 74 may be positioned within an opening on the second end wall 48.

The air circulation fan 34 generally moves air through the UV light generating unit 16 along an air flow path that includes, in order from input to output, the grill 70, the air filter 72, the air circulation fan 34, the second opening 58 in the first internal wall 50, the space surrounding the UV light source 32 between the first and second internal walls 50, 52, the first opening 60 in the second internal wall 52, and the vent 74.

The communication element 36 generally allows communication with external systems or devices. The communication element 36 may include signal or data transmitting and receiving circuits, such as antennas, amplifiers, filters, mixers, oscillators, digital signal processors (DSPs), and the like. The communication element 36 may establish communication wirelessly by utilizing radio frequency (RF) signals and/ or data that comply with communication standards such as cellular 2G, 3G, or 4G, Institute of Electrical and Electronics Engineers (IEEE) 802.11 standard such as WiFi, IEEE 802.16 standard such as WiMAX, Bluetooth™, or combinations thereof. In addition, the communication element 36 may utilize communication standards such as ANT, ANT+, Bluetooth™ low energy (BLE), the industrial, scientific, and medical (ISM) band at 2.4 gigahertz (GHz), or the like. Alternatively, or in addition, the communication element 36 may establish communication through connectors or couplers that receive metal conductor wires or cables which are compatible with networking technologies such as ethernet. In certain embodiments, the communication element 36 may also couple with optical fiber cables. The communication element 36 may be in communication with the processing element 40 and the memory element 38.

The memory element 38 may include data storage components such as read-only memory (ROM), programmable ROM, erasable programmable ROM, random-access memory (RAM) such as static RAM (SRAM) or dynamic RAM (DRAM), hard disks, floppy disks, optical disks, flash memory, thumb drives, universal serial bus (USB) drives, or the like, or combinations thereof. The memory element 38 may include, or may constitute, a "computer-readable medium". The memory element 38 may store the instructions, code, code segments, software, firmware, programs, applications, apps, services, daemons, or the like that are executed by the processing element 40. The memory element 38 may also store electronic data, settings, documents, sound files, photographs, movies, images, databases, and the like.

The processing element 40 may include processors, microprocessors, microcontrollers, digital signal processors (DSPs), field-programmable gate arrays (FPGAs), analog and/or digital application-specific integrated circuits (ASICs), or the like, or combinations thereof. The processing element 40 may generally execute, process, or run instructions, code, code segments, software, firmware, programs, applications, apps, processes, services, daemons, or the like. The processing element 40 may also include hardware components such as finite-state machines, sequential and combinational logic, and other electronic circuits that can perform the functions necessary for the operation of the current invention. The processing element 40 may be in communication with the other electronic components through serial or parallel links that include address busses, data busses, control lines, and the like.

The processing element 40 may receive the room occupancy signal from the room occupancy sensor 12, the door closed signal from the door sensor 14, and the shutter position signal from the shutter position sensor 30. The processing element 40 may also receive data, signals, codes, or instructions from the control software application 20, discussed in more detail below, that direct the processing element 40 to control the operation of the shutter motor 28, the UV light source 32, and the air circulation fan 34.

The processing element 40 may be programmed or configured to control the operation of the shutter motor 28 by generating data, signals, codes, or instructions that start and stop the shutter motor 28 in order to adjust the position of the shutter 26. The processing element 40 may be programmed or configured to control the operation of the UV light source 32 by generating data, signals, codes, or instructions that turn it on and off. The processing element 40 may be programmed or configured to control the operation of the air circulation fan 34 by generating data, signals, codes, or instructions that turn it on and off. The processing element 40 may control the operation of the shutter motor 28, the UV light source 32, and the air circulation fan 34 based on input from the room occupancy sensor 12, the door sensor 14, the shutter position sensor 30, the control software application 20, or combinations thereof.

Figure 12:
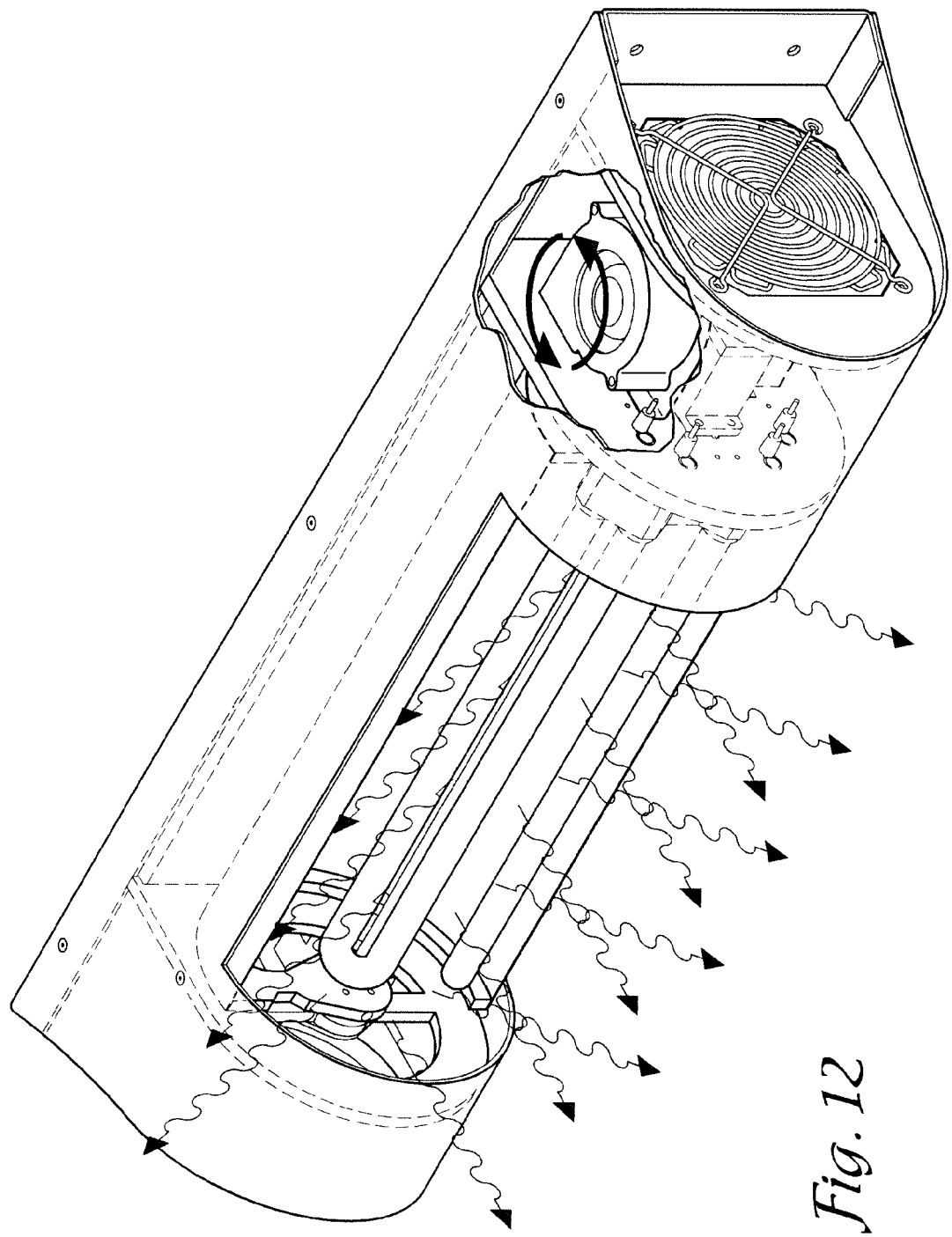
FIG. 12 is a perspective view of the UV light generating unit operating in an air and surface disinfection mode.

The UV light generating unit 16 may operate in one of four modes as controlled or directed by the control software application 20. A first mode may include air and surface disinfection, as shown in FIG. 12. The air circulation fan 34 and the UV light source 32 may be on, while the shutter 26 is fully open. Air may be moved through the air flow path by the air circulation fan 34, and the surfaces of objects in the enclosed space in the line of sight of the UV light source 32 may receive UV radiation therefrom. The UV light generating unit 16 may stay in the first mode as long as the room occupancy signal indicates that the enclosed space is unoccupied and the door closed signal indicates that the enclosed space door is closed, or as long as necessary to perform a sanitizing cycle.

Figure 13:
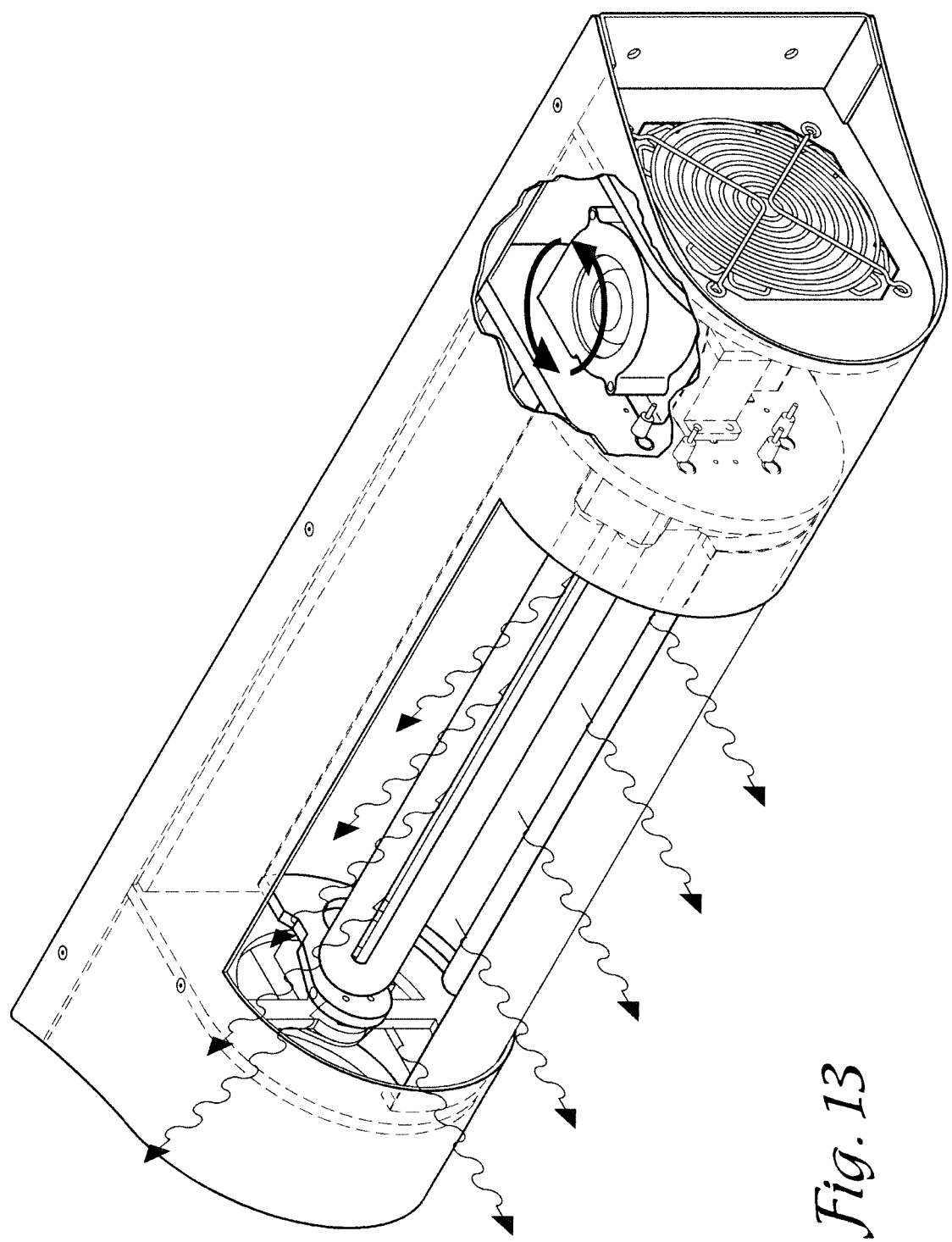
FIG. 13 is a perspective view of the UV light generating unit operating in an air and upper enclosed space disinfection mode.

A second mode may include air, upper enclosed space or room, and ceiling disinfection, or upper room irradiation, as shown in FIG. 13. The air circulation fan 34 and the UV light source 32 may be on, while the shutter 26 is halfway open, shown with the UV light generating unit 16 in isolation in FIG. 2. Air may be moved through the air flow path by the air circulation fan 34. With the shutter 26 open only roughly halfway, the ceiling, the upper portion of the walls, and objects in the upper portion of the enclosed space may receive UV radiation from the UV light source 32. The UV light generating unit 16 may switch to the second mode from the first mode if the room occupancy signal indicates that the enclosed space is occupied and/or the door closed signal indicates that the enclosed space door is open. The UV light generating unit 16 may return to the first mode if the room occupancy signal indicates that the enclosed space is unoccupied and the door closed signal indicates that the enclosed space door is closed. The UV light generating unit 16 may also be programmed to operate in the second mode for a predetermined period of time. The UV light generating unit 16 may operate in the second mode while the enclosed space is occupied only if it is safe to do so, such as when the UV light generating unit 16 can be positioned on a wall well above head level of any humans occupying the enclosed space and if there are no reflective objects or surfaces on the ceiling.

Figure 14:
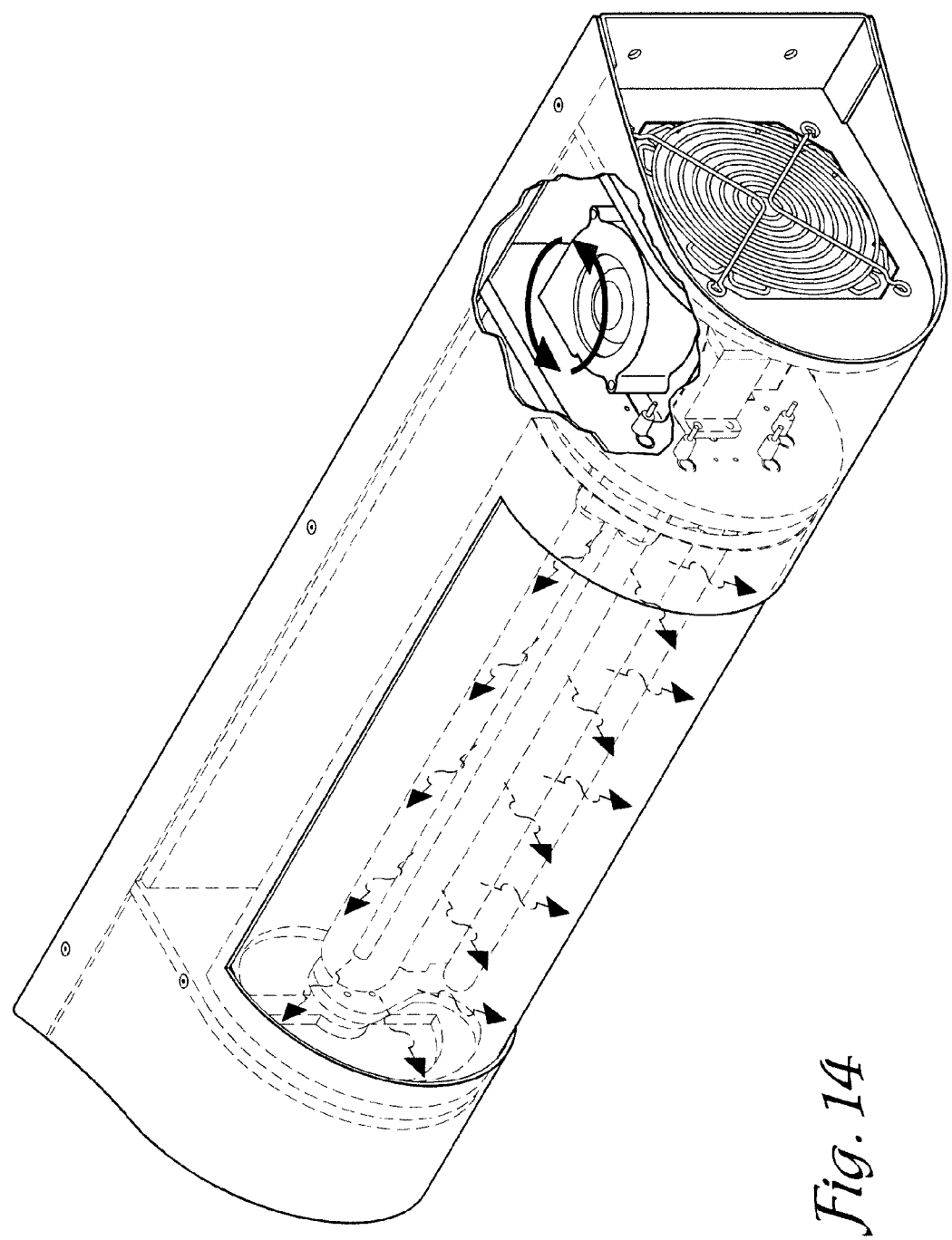
FIG. 14 is a perspective view of the UV light generating unit operating in an air disinfection only mode.

A third mode may include air disinfection only, as shown in FIG. 14. The air circulation fan 34 and the UV light source 32 may be on, while the shutter 26 is closed, shown with the UV light generating unit 16 in isolation in FIG. 3. Air may be moved through the air flow path by the air circulation fan 34. The UV light generating unit 16 may switch to the third mode from the first mode if the room occupancy signal indicates that the enclosed space is occupied and/or the door closed signal indicates that the enclosed space door is open, and if it is not safe to operate in the second mode. The UV light generating unit 16 may return to the first mode if the room occupancy signal indicates that the enclosed space is unoccupied and the door closed signal indicates that the enclosed space door is closed. The UV light generating unit 16 may also be programmed to operate in the third mode for a predetermined period of time.

Figure 15:
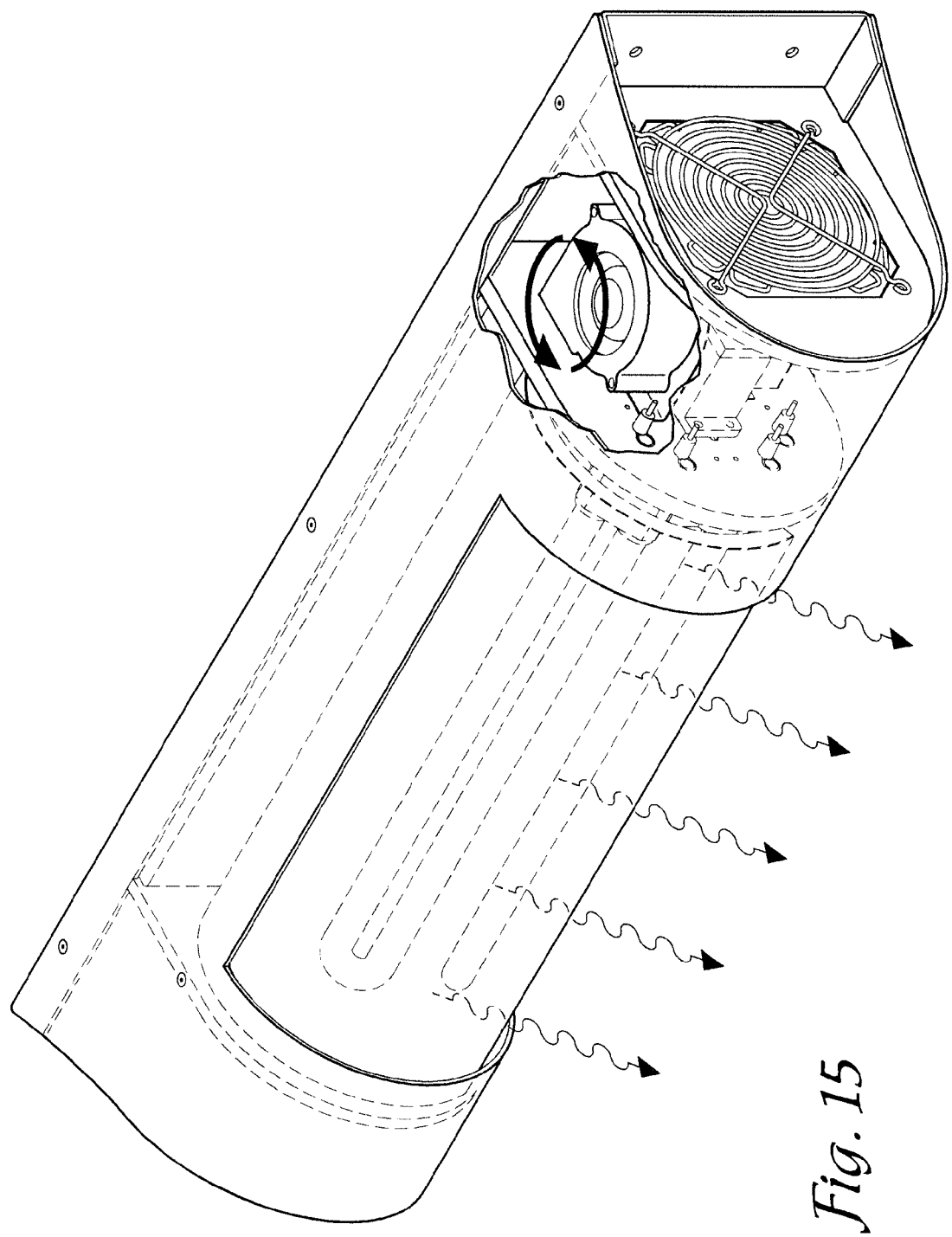
FIG. 15 is a perspective view of the UV light generating unit operating in an air and entry-way disinfection mode.

A fourth mode may include entry-way sanitization in which the UV light generating unit 16 provides a sterile barrier to an entry-way into the enclosed space, as shown in FIGS. 15 and 16. The fourth mode of operation may be a specialized usage of the UV light generating unit 16 because it requires that the UV light generating unit 16 be placed directly over a doorway that provides access to the enclosed space. Furthermore, in the fourth mode, the air circulation fan 34 and the UV light source 32 are on, but the shutter 26 may open only a small amount to generate a narrow beam of UV radiation that is aimed downward from the UV light generating unit 16 across the doorway to the floor. The shutter 26 may close all the way when the door closed signal indicates that the enclosed space door is open, but the shutter 26 may open again a small amount once the door closed signal indicates that the enclosed space door is closed. The shutter 26 may remain open a small amount while the room is occupied since the narrow UV radiation beam should not be directly incident upon any humans present in the enclosed space. While the fourth mode of operation provides beneficial sterilization of microorganisms as they try to enter the enclosed space through the doorway, the UV light generating unit 16 may not necessarily provide sanitization of other surfaces or spaces in the enclosed space due to the narrow opening of the shutter 26.

Figure 8:
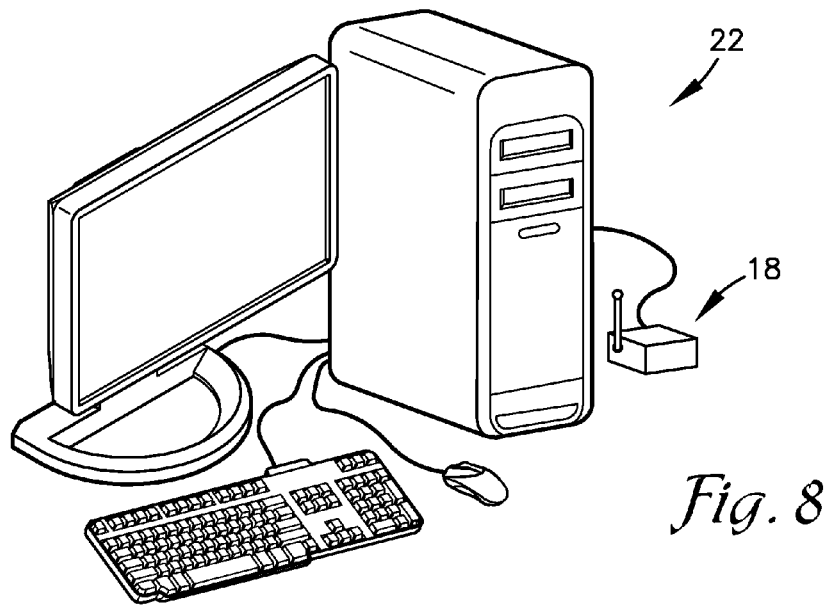
FIG. 8 is a perspective view of a computing device that interfaces with the UV light germicidal sanitizing system utilizing a base station transceiver.
Figure 9:
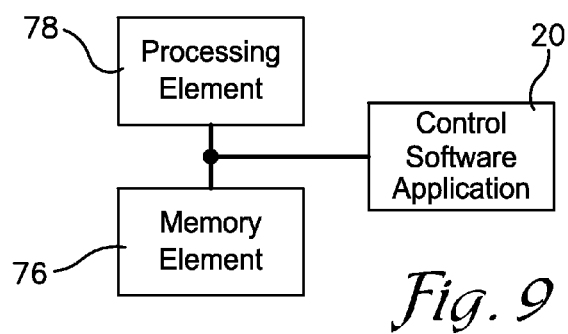
FIG. 9 is a schematic block diagram of components of the computing device.

The base station transceiver 18, shown in FIG. 8, generally provides communication between the communication element 36 of the UV light generating unit 16 and the computing device 22 that is executing the control software application 20. The base station transceiver 18 may include signal or data transmitting and receiving circuits, such as antennas, amplifiers, filters, mixers, oscillators, DSPs, and the like. With the communication element 36, the base station transceiver 18 may establish communication wirelessly by utilizing RF signals and/or data that comply with communication standards such as cellular 2G, 3G, or 4G, IEEE 802.11 standard such as WiFi, IEEE 802.16 standard such as WiMAX, Bluetooth™, or combinations thereof. With the computing device 22, the base station transceiver 18 may establish communication through metal conductor wires or cables that connect to a communication port on the computing device 22, such as the USB port.

The computing device 22, shown in FIG. 8, which executes the control software application 20 may include workstation computers, desktop computers, laptop computers, palmtop computers, notebook computers, tablets or tablet computers, smartphones, mobile phones, personal digital assistants (PDAs), or the like. The computing device 22 may further include a memory element 76 and a processing element 78, similar in structure to the memory element 38 and the processing element 40, respectively. The memory element 76 may store the control software application 20, while the processing element 40 may execute the control software application 20. The computing device 22 may further include a display and user interface components such as a keyboard and a mouse. In various embodiments, the base station transceiver 18 may be integrated in the same housing as the computing device 22, such as in the case of a smartphone or other handheld device.

The control software application 20 generally provides a programmable interface for a user to control the operation of the UV light generating unit 16 and may include data, instructions, code, code segments, or the like directed to that function. The control software application 20 may allow the user to schedule sanitizing periods for a seven-day schedule. In some scenarios, the facility that includes the enclosed space in which the UV light generating unit 16 is utilized may have fixed hours of operation. The hours may be different on the weekends than they are for weekdays. During the hours when the facility is not operating, it may be unoccupied and thus, the user may schedule a sanitizing period to begin when the facility is known to be unoccupied. The user may schedule a time for the sanitizing period to begin for each day of the week. In some embodiments, the user may also schedule the UV light generating unit 16 to shut off, such that the UV light source 32 and the air circulation fan 34 are off and the shutter 26 is fully closed, during holidays or extended periods of inactivity for the facility.

The sanitizing period may include setting the UV light generating unit 16 in the first mode of operation for a first period of time. Since the sanitizing period is scheduled for when the facility is known to be unoccupied, the UV light generating unit 16 may operate in the first mode without interruption. The value of the first period of time may depend on variables such as the output power of the UV light source 32, the type of microorganisms that are to be neutralized by the UV light generating unit 16, the dimensions of the enclosed space, the type of textures of materials in the enclosed space, the amount or degree of degradable materials in the enclosed space, and the like. The output power of the UV light source 32 may be entered at the time of assembly of the UV light generating unit 16 or it may be entered by the user. Each type of microorganism to be neutralized may require a certain dose of UV exposure in order to inhibit colony formation. The dose may be determined from laboratory experimental or empirical data and may be expressed as a time power per area. In international system units, the dose may be expressed in microwatt seconds per square centimeter. This information may be prestored in the memory element 76, or it may be entered by the user, if known. The remaining variable data may be entered by the user, and the first period of time may be calculated by the control software application 20.

As an example, if the control software application 20 determines that for a particular enclosed space the first time period is 3 hours, then, at a time of day determined by the user, the control software application 20 may instruct the UV light generating unit 16 to run in the first operating mode for 3 hours. Afterward, the control software application 20 may instruct the UV light generating unit 16 to turn the UV light source 32 and the air circulation fan 34 off and close the shutter 26.

The user may use the control software application 20 to schedule the UV light generating unit 16 to operate in the first mode once the facility is operating again. The UV light generating unit 16 may switch to the second or third mode whenever the room occupancy signal indicates that the enclosed space is occupied and/or the door closed signal indicates that the enclosed space door is open. If the enclosed space remains unoccupied and the UV light generating unit 16 runs in the first mode uninterrupted, or briefly interrupted, for a period of time equal to the sanitizing period, then the UV light generating unit 16 may shut off until the enclosed space is occupied again. Alternatively, if the enclosed space remains unoccupied for an extended period of time, the control software application 20 may instruct the UV light generating unit 16 to operate in the first mode for a predetermined period of time, such as 30 minutes, and then shut off.

The control software application 20 may receive status information from the UV light generating unit 16 at regular intervals. Typically, the control software application 20 receives the on/off status of the UV light source 32 and the air circulation fan 34, the position of the shutter 26, and the state of the room occupancy signal and the door closed signal. The control software application 20 may store the status information in the memory element 76.

The UV light germicidal sanitizing system 10 may operate as follows. One or more room occupancy sensors 12 may be set up in the enclosed space to monitor for human or animal occupancy. The door sensor 14 may be installed on the door, or doors, that provide access to the enclosed space. The UV light generating unit 16 may be mounted on one of the walls in the enclosed space close to the ceiling and preferably in a centralized location, as generally shown in FIG. 1. The base station transceiver 18 may be connected to the computing device 22 on which the control software application 20 is running. The computing device 22 may be located within the enclosed space, or in another location, such that the base station transceiver 18 is within signal range of the UV light generating unit 16.

The user may access the control software application 20 to schedule the operation of the UV light generating unit 16. The user may schedule a sanitizing period as well as default operating modes for each day of the week. Once the user has entered and saved the schedule, the control software application 20 may communicate with the UV light generating unit 16 through the base station transceiver 18 connected to the computing device 22. The control software application 20 may send operating commands to the UV light generating unit 16 and may receive status information therefrom. Typically, once the UV light generating unit 16 has received initial instructions from the control software application 20 regarding operating mode, the UV light generating unit 16 may operate independently or autonomously, switching operating modes based on the signals from the sensors 12, 14, until the next event scheduled by the user, such as a sanitizing period or a shut off of the UV light generating unit 16. At that time, the control software application 20 may send commands to the UV light generating unit 16 to perform the scheduled operation.

Figure 10:
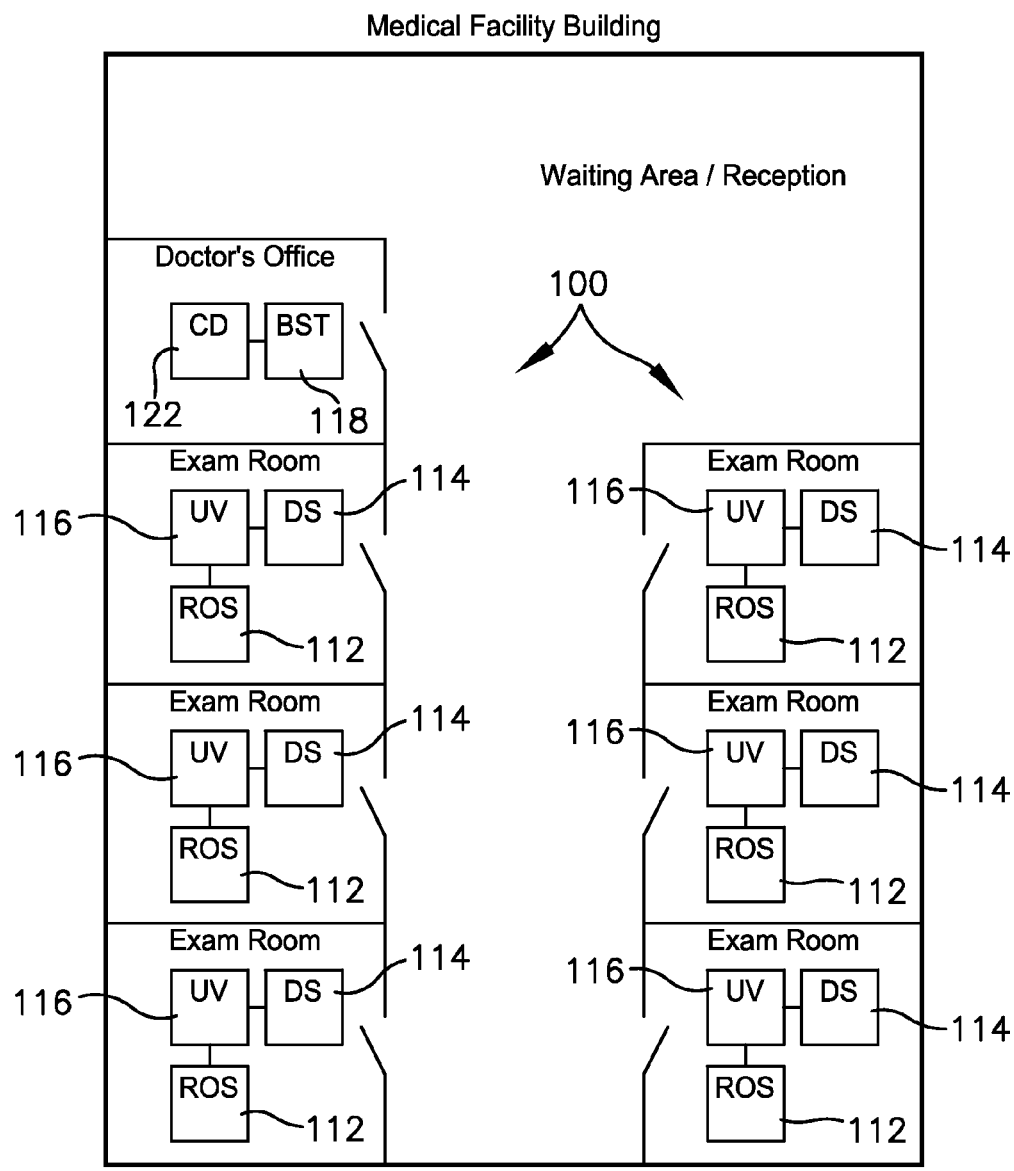
FIG. 10 is a schematic block diagram of a second embodiment of the UV light germicidal sanitizing system overlayed on a floor plan of a medical facility building.

A second embodiment of a UV light germicidal sanitizing system 100 may be shown in FIG. 10 and may broadly comprise a plurality of room occupancy sensors 112, a plurality of door sensors 114, a plurality of UV light generating units 116, a base station transceiver 118, and a control software application 120. The system 100 may interface with a computing device 122 that executes the control software application 120. The system 100 is typically utilized in a facility with multiple spaces that need germicidal sanitizing, such as doctor's offices with multiple exam rooms, medical clinics, hospitals, nursing homes, schools, dormitories, public buildings, public restrooms, transportation hubs, and the like.

Each room occupancy sensor 112, each door sensor 114, each UV light generating unit 116, and the base station transceiver 118 may be similar in structure and function to the like-named components discussed above for the UV light germicidal sanitizing system 10.

The UV light generating unit 116 may be substantially similar in structure and function to the UV light generating unit 16 discussed above, with the exception that the communication element of the UV light generating unit 116 may also be operable to send and receive commands, data, signals, codes, or instructions to the communication elements of other UV light generating units 116 as well as the base station transceiver 118. In addition, each UV light generating unit 116 may be assigned a unique identifier such as an address. During operation of the system 100, each UV light generating unit 116 may receive commands that include an address of a specific UV light generating unit 116. Each UV light generating unit 116 may follow the commands that include the address of the particular UV light generating unit 116 and may transmit or repeat the commands that include the addresses of other UV light generating units 116. Thus, the UV light generating units 116 may form a wireless network with individually addressable units once they are implemented in a facility.

Figure 11:
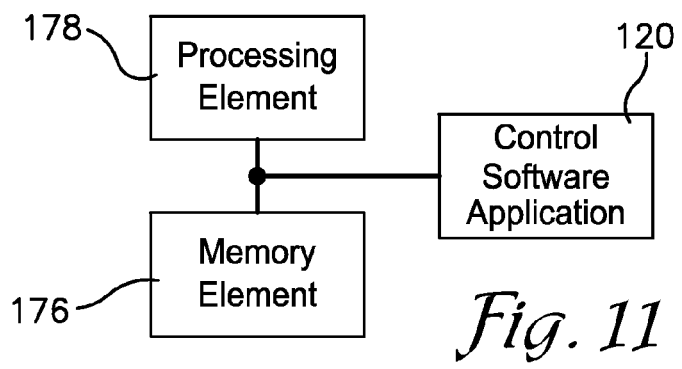
FIG. 11 is a schematic block diagram of components of a computing device that interfaces with the second embodiment of the UV light germicidal sanitizing system.

The computing device 122, indicated in FIGS. 10 and 11, may be similar in structure and function to the computing device 22 and may include a memory element 176 and a processing element 178. The control software application 120 may be similar in function to the control software application 20, except that the control software application 120 may allow the user to schedule the operation of all of the UV light generating units 116. The user may enter the operating parameters for each UV light generating unit 116 or a block of UV light generating units 116 for a seven-day schedule. In addition, the control software application 120 may include a unique identifier, such as an address, in the commands, instructions, or signals for each UV light generating unit 116. In various embodiments, the control software application 120 may be able to support or address up to 250 UV light generating units 116. Alternatively, the control software application 120 may encode the commands, instructions, or signals for each UV light generating unit 116. Furthermore, each UV light generating unit 116 may transmit data back to the control software application 120, wherein the data includes an address that identifies the source UV light generating unit 116.

An exemplary embodiment of the UV light germicidal sanitizing system 100, as shown in FIG. 10, may be utilized in a medical facility building that includes a waiting and reception area, a doctor's office, and six exam rooms. In FIG. 10, the room occupancy sensor 112 may be abbreviated as "ROS", the door sensor 114 may be abbreviated as "DS", the UV light generating unit 116 may be abbreviated as "UV", the base station transceiver 118 may be abbreviated as "BST", and the computing device 122 may be abbreviated as "CD". A combination of one room occupancy sensor 112, one door sensor 114, and one UV light generating unit 116 may be implemented in each exam room. The base station transceiver 118 and the computing device 122 that is executing the control software application 120 may be located in the doctor's office.

The system 100 may operate as follows. The control software application 120 may be set up by the user as described above and may generate commands for each UV light generating unit 116 based on the user-defined scheduling. The commands are broadcast by the base station transceiver 118. In the exemplary system 100 of FIG. 10, the base station transceiver 118 may communicate directly with the UV light generating units 116 that are closest to the doctor's office, but the UV light generating units 116 at the end of the building may be out of signal range of the base station transceiver 118. When the control software application 120 wants to transmit a command to the UV light generating units 116 that are farthest away, the base station transceiver 118 transmits the command to the closest UV light generating units 116. Those units 116 recognize that the command is not for them so they transmit the command themselves. Each UV light generating unit 116 may receive the command and re-transmit it until the intended UV light generating unit 116 receives the command and follows it. Each UV light generating unit 116 may operate in the first, second, or third mode, as described above for the UV light generating unit 16, once it receives commands or instructions from the control software application 120.

Each UV light generating unit 116 may also transmit status data back to the control software application 120. The data may not only include the address of the source UV light generating unit 116, but also may include the address of the base station transceiver 118 or the computing device 122, which is the destination for the data. Thus, the data generated by any one of the UV light generating units 116 is transmitted by the other UV light generating units 116 until it is received by the base station transceiver 118. The control software application 120 may store the status data from the UV light generating units 116 in the memory element 176.

The exemplary embodiment of the system 100 is shown in FIG. 10 being implemented in a single story facility. However, the system 100 may be implemented using a similar architecture in large-scale facilities, such as hospitals, with multi-story buildings. The computing device 122 running the control software application 120 may be located on the first floor (or any other floor) of the building while the UV light generating units 116 are installed on every floor throughout the building. The base station transceiver 118 may communicate with the UV light generating units 116 within signal range and those UV light generating units 116 may communicate with the UV light generating units 116 out of signal range on the same floor and other floors.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. An ultraviolet (UV) light generating unit for use in an enclosed space, the UV light generating unit comprising:
    a housing including a base plate and a shell, the base plate having opposing edges, the shell having a curved semi-cylindrical portion, planar sidewalls attached to the opposing edges of the base plate, and an aperture along the curved semi-cylindrical portion, the housing being configured to be mounted above a doorway of the enclosed space;
    a shutter having a semi-cylindrical shape and being rotatable between a first position in which the shutter covers the aperture and a second position in which the shutter exposes a majority of the aperture;
    a motor configured to rotate the shutter between the first and second positions;
    a UV light source positioned within the housing and configured to generate radiation in the UVC band of the electromagnetic radiation spectrum and transmit the radiation through the aperture when the shutter is in the second position;
    a fan positioned within the housing and configured to move air from outside of the housing in and through a first opening in the housing, past the UV light source, and out of a second opening in the housing;
    a memory element configured to store electronic data; and
    a processing element electronically coupled with the memory element and configured to
    operate the UV light generating unit in one of four modes:
        i) air and surface disinfection mode, wherein the fan is on, the UV light source is generating radiation, and the shutter is in the second position such that radiation emanates towards a ceiling and towards a floor of the enclosed space;
        ii) air and upper enclosed space disinfection mode, wherein the fan is on, the UV light source is generating radiation, and the shutter is between the first position and the second position such that the UV radiation emanates towards a ceiling and upper portion of walls of the enclosed space from above the doorway;
        iii) air disinfection only mode, wherein the fan is on, the UV light source is generating radiation, and the shutter is in the first position such that UV light sterilizes air blown through the unit by the fan; and
        iv) air and entry-way disinfection mode, wherein the fan is on, the UV light source is generating radiation, and the shutter is positioned such that the UV light generating unit creates a narrow beam of radiation aimed downward from the UV light generating unit along the doorway towards the floor of the enclosed space.

2. The UV light generating unit of claim 1, further comprising a shutter position sensor configured to determine whether the shutter is in the first position or in the second position.

3. The UV light generating unit of claim 1, wherein the shell has an inner surface and the shutter has an outer surface with a smaller radius of curvature than the inner surface of the shell, the outer surface of the shutter being positioned adjacent to the inner surface of the shell.

4. An ultraviolet (UV) light germicidal sanitizing system for use in an enclosed space, the system comprising:
    a plurality of room occupancy pressure sensors configured to detect weight of a room occupant and to generate a first signal indicating that the enclosed space is either occupied or unoccupied;
    a motion detector sensor configured to detect motion of the room occupant and to generate a second signal indicating that the enclosed space is either occupied or unoccupied;
    a door sensor configured to be implemented with a door providing access to the enclosed space and to generate a third signal indicating that the door is either open or closed;
    a UV light generating unit configured to be mounted above a doorway of the enclosed space, the UV light generating unit including:
        a housing including a shell with an aperture;
        a shutter movable between a first position in which the shutter covers the aperture and a second position in which the shutter exposes a majority of the aperture;
        a fan positioned within the housing and configured to move air from outside of the housing in and through a first opening in the housing, past the UV light source, and out of a second opening in the housing;
        a UV light source positioned within the housing and configured to generate radiation in the UVC band of the electromagnetic radiation spectrum through the aperture when the shutter is in the second position, the UV light generating unit being configured to operate in one of four modes:
            i) air and surface disinfection mode, wherein the fan is on, the UV light source is generating radiation, and the shutter is in the second position such that radiation emanates towards a ceiling and towards a floor of the enclosed space;
            ii) air and upper enclosed space disinfection mode, wherein the fan is on, the UV light source is generating radiation, and the shutter is between the first position and the second position such that the UV radiation emanates towards a ceiling and upper portion of walls of the enclosed space from above the doorway;

iii) air disinfection only mode, wherein the fan is on, the UV light source is generating radiation, and the shutter is in the first position such that UV light sterilizes air blown through the unit by the fan; and iv) air and entry-way disinfection mode, wherein the fan is on, the UV light source is generating radiation, and the shutter is positioned such that the UV light generating unit creates a narrow beam of radiation aimed downward from the UV light generating unit along the doorway towards the floor of the enclosed space;

a memory element configured to store electronic data; and a processing element electronically coupled with the memory element and configured to:

receive the first signal, the second signal, and the third signal, and generate a fourth signal to be used to move the shutter to the first position when the first signal or the second signal indicates that the enclosed space is occupied or the third signal indicates that the door is open and to the second position when the first signal and the second signal indicate that the enclosed space is unoccupied and the third signal indicates that the door is closed such that the UV light generating unit operates in the air and surface disinfection mode if the first signal and the second signal indicate that the enclosed space is unoccupied and the third signal indicates that the door is closed;

a base station transceiver configured to provide wireless communication with the UV light generating unit; and a control software application configured to execute on a computing device that is coupled with the base station transceiver and to generate a first operating command for the UV light generating unit to start generating UV light and a second operating command for the UV light generating unit to stop generating UV light.

5. The UV light germicidal sanitizing system of claim 4, wherein the control software application is further configured to calculate a sanitizing period of time during which the UV light generating unit generates UV light into the enclosed space without interruption and to generate the second operating command after the sanitizing period of time has elapsed.

6. The UV light germicidal sanitizing system of claim 4, wherein the UV light generating unit further includes a motor which receives the fourth signal and moves the shutter between the first position and the second position.

7. The UV light germicidal sanitizing system of claim 4, wherein the UV light generating unit further includes a shutter position sensor configured to determine whether the shutter is in the first position or in the second position.

8. The UV light germicidal sanitizing system of claim 4, wherein the UV light generating unit further includes a communication element to communicate with the base station transceiver.

9. The ultraviolet (UV) light generating unit of claim 1, wherein the unit is configured to operate in mode ii) for a predetermined period of time.

10. The ultraviolet (UV) light generating unit of claim 1, wherein the unit is configured to operate in mode iii) for a predetermined period of time.

11. The ultraviolet (UV) light generating unit of claim 1, wherein the processing element is configured to receive operating commands from other UV light generating units and transmit operating commands to other UV light generating units.

* * * * *